United States Patent [19]

Henderson

[11] Patent Number: 4,955,717

[45] Date of Patent: Sep. 11, 1990

[54] DEMAND MODULATED ATOMIZATION APPARATUS AND METHOD FOR PLASMA SPECTROSCOPY

[75] Inventor: William B. Henderson, Torrance, Calif.

[73] Assignee: Geochemical Services, Inc., Torrance, Calif.

[21] Appl. No.: 376,228

[22] Filed: Jun. 29, 1988

Related U.S. Application Data

[63] Continuation of Ser. No. 178,896, Mar. 31, 1988, abandoned, which is a continuation-in-part of Ser. No. 936,837, Dec. 2, 1986, abandoned.

[51] Int. Cl.$^5$ ........................................... G01N 21/73
[52] U.S. Cl. ..................................... 356/316; 250/288
[58] Field of Search ................. 356/36, 311, 312, 313, 356/315, 316, 318, 417; 250/288

[56] References Cited

U.S. PATENT DOCUMENTS

| | | | |
|---|---|---|---|
| 3,396,303 | 8/1968 | Gordon | 356/313 |
| 4,256,404 | 3/1981 | Walker | 356/316 |
| 4,314,764 | 2/1982 | Liddell et al. | 356/315 |
| 4,556,318 | 12/1985 | Barnes et al. | 356/316 |
| 4,615,225 | 10/1986 | Sainz | 356/316 |
| 4,684,251 | 8/1987 | Brouwer et al. | 356/315 |

FOREIGN PATENT DOCUMENTS

| | | | |
|---|---|---|---|
| 3307409 | 9/1984 | Fed. Rep. of Germany | 356/315 |
| 2122342 | 1/1984 | United Kingdom | 356/316 |

OTHER PUBLICATIONS

Applied Spectroscopy, vol. 39, No. 4, Jul.-Aug. 1985, Society for Applied Spectroscopy (Frederick, Maryland, U.S.) pp. 719-726.

TRAC, Trends in Analytical Chemistry, vol. 2, No. 10, Oct. 1983, Elsevier Science Publishers B.V. (Cambridge, GB) pp. 225-230.

Analytical Chemistry, vol. 56, No. 11, Sep. 1984, American Chemical Society, (Easton, PA, U.S.) 1997-2000.

Analytical Chemistry, vol. 58, No. 1, Jan. 1986, American Chemical Society, (Washington, U.S.) pp. 97A-105A.

Matusiewicz et al, Applied Spectroscopy, vol. 38, No. 5, Sep./Oct. 1984, pp. 745-747.

Primary Examiner—F. I. Evans
Attorney, Agent, or Firm—Spensley Horn Jubas & Lubitz

[57] ABSTRACT

A demand modulated electrothermal atomization plasma spectroscopy system intended to reliably and controllably atomize samples. The invention is used in conjunction with a plasma spectroscopic instrument, and includes a feedback control loop that monitors the rate of analyte consumption in a plasma torch and regulates the temperature of an electrothermal atomization means that supplies analyte material to the plasma torch. The feedback system in the preferred embodiment regulates atomization temperature based upon ion or photon count rates.

19 Claims, 3 Drawing Sheets

DEMAND MODULATED ATOMIZATION APPARATUS AND METHOD FOR PLASMA SPECTROSCOPY

This is a continuation of application Ser. No. 6/936,837 filed on Dec. 2, 1986, now abandoned.

BACKGROUND OF THE INVENTION

1. Field of the Invention

This invention relates to control systems for spectroscopic devices, and more particularly, to a demand modulated atomization system particularly adapted for use in plasma spectroscopy.

2. Background Information

In atomic absorption spectroscopy, atomic fluorescence spectroscopy, and atomic emission spectroscopy, a means must be provided to atomize a source of sample material so that the sample's absorption, fluorescence, or emission spectra may be observed. In the past, atomization has been accomplished by using a nebulizer or an electrothermal atomizer. Various aspects of the work in the area of electrothermal atomization have been patented. (See, for example, U.S. Pat. No. 4,407,582 to Woodriff, issued Oct. 4, 1983, and U.S. Pat. No. 4,529,307 to Holcomb, et al., issued Jul. 16, 1985).

During the 1970's, a new analytical technique known as inductively coupled plasma (ICP) emerged. A plasma is defined as a luminous gas, a significant fraction of whose atoms or molecules are ionized. Plasmas therefore are considered to be gaseous conductors. As such, plasmas readily interact with magnetic fields, making it possible to couple a plasma to a high frequency power source. The emergence of ICP techniques led to the wide spread use of ICP atomic emission spectroscopy systems. ICP atomic fluorescence spectroscopy systems have also been developed. (See for example, U.S. Pat. No. 4,300,834 to Demers, et al., issued Nov. 17, 1981).

Even with use of an ICP technique, some means must be used to introduce analyte (that is, the material to be analyzed) to the ICP system (commonly known as a "torch"). One such means is a nebulizer, which introduces a mist of liquid or dissolved analyte to the ICP torch. This has the disadvantage of limiting the types and concentrations of analyte that may be examined.

An electrothermal atomization device may also be used to provide atomized samples of test material for injection into an ICP torch. In the past, all such systems known to the inventor produce transient signals dependent on conditions pre-set by an operator. This requires a knowledge of the contents of the sample being tested and is not compatible with high volume production work where such prior knowledge is not practical, and where concentrations of various elements may vary over many orders of magnitude. Furthermore, presently existing ICP spectroscopy instruments provide poor control of the rate of production of ions of any and all elements present in a sample, and are frequently limited in the types of materials that can be used as a sample. For example, many such ICP spectroscopic instruments are unable to test samples comprising solid material, or solutions containing high amounts of dissolved solids. In other prior art instruments, such samples can be tested only by reconfiguring the entire instrument, which can be a time-consuming task if precise measurements are to be obtained.

In examining the prior art, it has been discovered that a major problem in obtaining adequate results in commercially viable instruments has been an inability to accurately control the atomization rate of sample material being injected into an ICP torch. This is especially true in the recently developed technique known as ICP-/Mass spectroscopy. It is therefore highly desirable that some means or method be developed that accurately controls the analyte atomization rate.

SUMMARY OF THE INVENTION

The present invention is a demand modulated electrothermal atomization system for use in a spectroscopy system, particularly an ICP spectroscopy system, and is intended to reliably and controllably atomize samples for high volume production for use in ICP spectroscopy. The technique and apparatus developed extend the linear dynamic range of ICP spectroscopy and improve the counting statistics of an ICP spectroscopy instrument by automatically controlling the amount of analyte entering the plasma torch. Furthermore, the inventive apparatus and technique permit adding the measurement of volitization temperature to the data produced by the instrument, which has important implications for "finger-printing" samples and for analyzing molecular compounds containing various elements.

The present invention in its preferred embodiment comprises an ICP spectroscopic instrument employing a feedback control loop that monitors the rate of analyte consumption in an ICP torch and regulates the temperature of an electrothermal atomization furnace that supplies analyte material to the ICP torch. The feedback system in the preferred embodiment regulates atomization temperature based upon ion or photon count rates.

The feedback controller may be implemented in a number of ways. A particular electronic feedback control system is disclosed herein, but numerous variations of the inventive concept would be readily devisable by persons skilled in the relevant arts upon reference to this disclosure.

The present invention has the advantage of reducing the atomizer noise level compared to the prior art, thereby improving measurement precision. It also has the advantage of maintaining relatively constant ion count rates, so that the ICP instrument may be more useful for isotope ratio determinations.

Another advantage of the present invention is that high dissolved solids samples can be more accurately analyzed, since the atomization rate is more carefully controlled. This is especially useful for minimization of sampler cone clogging and matrix suppression effects in ICP mass spectrographic instruments. (For example, masking by high concentration, easily ionizable constituent elements of trace constituent elements with higher ionization potentials).

Yet another advantage of the present invention is extension of the linear dynamic range of an ICP spectroscopic instrument by not allowing ion or photon count rates to enter the non-linear regions of the detection and analysis instruments. This is especially important in fields such as geochemical analysis, since there is usually little known about a sample's content prior to analysis and concentrations of various components may vary by many orders of magnitude. By carefully controlling the atomization rate of an analyte, the linear dynamic range of the instrument is in effect extended by several orders of magnitude. The present invention makes possible accurate analysis of samples containing constituent elements comprising anywhere from parts per billion to parts per hundred in a single pass without the need for dilution.

The invention will become more readily understood by reference to the description of the preferred embodiment set forth below, in conjunction with the accompanying drawings.

BRIEF DESCRIPTION OF THE DRAWINGS

Like reference numbers in the various drawings represent like elements.

DETAILED DESCRIPTION OF THE INVENTION

Figure 1:
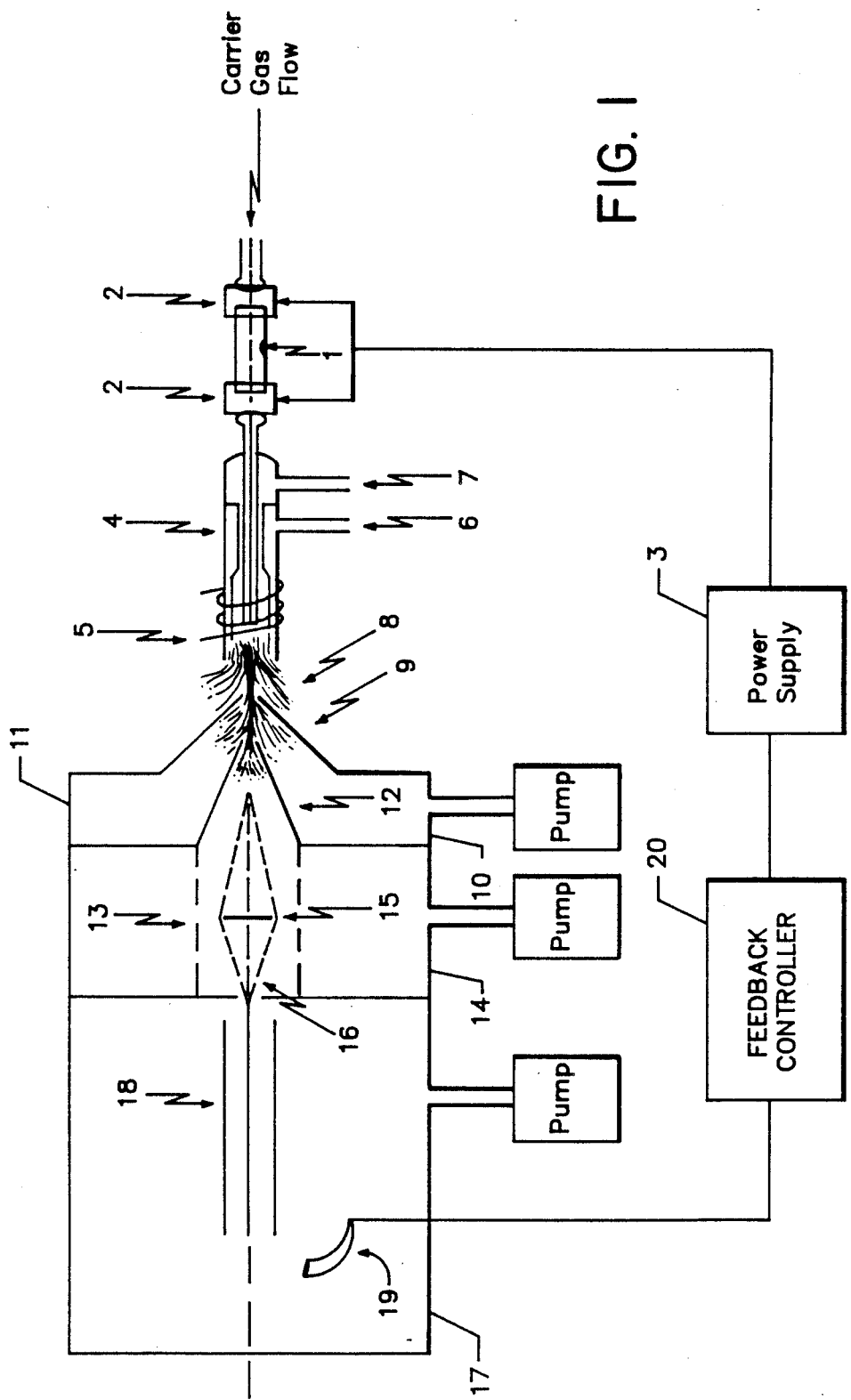
FIG. 1 is a schematic diagram of an inductively coupled plasma emission spectroscopy instrument employing the inventive demand modulated electrothermal atomization apparatus and method of the present invention.

FIG. 1 discloses a schematic diagram of an inductively coupled plasma mass spectroscopic instrument employing the feedback control method and apparatus of the present invention. An equivalent drawing can be made for an ICP emission or fluorescence spectroscopic system or a gas-flame atomic absorption spectroscopic system. In one embodiment, a graphite (or other refractory material) sample tube 1 containing a test sample is placed between water-cooled electrically conductive electrodes in an electrothermal furnace 2, and coupled to an electronically-controllable power supply 3. The power supply 3 is of sufficient size so as to raise the temperature of the analyte in the sample tube 1 to a temperature sufficient to atomize a desired component of the test sample. A flow of a carrier gas (such as argon) is provided to flow through the sample tube 1 and carry atomized molecules through an inner tube of an inductively coupled plasma torch 4. The ICP torch 4 of the illustrated embodiment can generate an atmospheric pressure plasma at a temperature of approximately 7000° K., which is sufficient to ionize a substantial fraction of any elements present in the carrier gas flow. The plasma itself is generated by means of a radio frequency (RF) inductive coil 5 surrounding the ICP torch 4. The residence time of the carrier gas in the ICP torch 4 is such that the injected gas from the electrothermal furnace 2 approaches the temperature of the plasma, at which most molecules are broken down into ionized atoms.

In one the illustrated embodiment of the ICP torch 4, a coolant is admitted to the ICP torch to a surrounding coolant space 6. In addition, an auxiliary flow of a second carrier gas may be admitted into the ICP torch 4 through an auxiliary opening 7 in order to increase the separation of the plasma from the injection tip of the ICP torch 4.

The outrush of ionized sample-laden plasma 8 from the ICP torch 4 impinges upon a sampler cone 9, which contains an opening permitting a portion of the plasma flow 8 to enter into the first stage 10 of a differentially pumped vacuum chamber 11. In the illustrated embodiment, the first stage 10 of the vacuum chamber 11 is pumped to a partial vacuum of approximately 10° torr.

The impingement of the plasma flow 8 upon the sampler cone 9 and the rapid expansion of the portion of the plasma flow that passes through the sampler cone 9 and on into the first stage 10 of the vacuum chamber 11 causes the admitted ions to "freeze" and remain in plasma form rather than coalescing out of the plasma state.

A fraction of the "frozen" ions are further selected by means of a skimmer cone 12 within the interior of the first stage 10 of the vacuum chamber 11. In the illustrated embodiment, positively charged ions that pass through the skimmer cone 12 are extracted by a means of an ion lens system 13 in a second stage 14 of the differentially pumped vacuum chamber. The second stage 14 in the illustrated embodiment is pumped to a partial vacuum of approximately $5 \times 10^{-4}$ torr. A photon stop shield 15 is provided to prevent light generated by the ICP torch 4 from passing further into the vacuum chamber 11, where measuring instruments may be damaged or affected by the photon beam.

The ion lens system 13 focuses the extracted positively charged ion flow 16 into a third stage 17 of the vacuum chamber 11. This third stage is pumped to a partial vacuum of approximately $5 \times 10^{-6}$ torr in the illustrated embodiment. The ion flow 16 is directed into a quadrapole mass spectrometer 18. This device acts like a selective filter, allowing only ions having a distinct mass/charge ratio to pass at any instant of the electronic scan. The electronic scan of the quadrapole mass spectrometer 18 is synchronized with a detector 19, such as a Channeltron detector manufactured by the Galileo Electro-Optics Corp., Galileo Park, Sturbridge, Mass., allowing data to be collected in the form of ion counts versus atomic mass units.

The output of the ion detector 19 is coupled to a feedback controller circuit 20, which in turn is coupled to the controllable power supply 3. The feedback controller circuit 20 compares the integrated ion count during a particular time period to a pre-set limit. If the count equals or exceeds the preset limit, that fact indicates that the flow rate of ions from the electrothermal furnace 2 is excessive at that unique mass/charge ratio and the controller is not advanced to the next power step. If the ion count rate is less than the preset limit, the ion flow rate is increased by advancing the power supply 3 to the next power step, which causes an increase in temperature of the electrothermal furnace 2. This feedback process continues until the electrothermal furnace 2 reaches a preset target temperature, which may be calibrated in terms of a preset power input to the feedback controller 20. The input power may be set as a percentage of the total power available for powering the electrothermal furnace 2.

In the illustrated embodiment, once the preset maximum ion flow rate or preset target temperature is reached, the temperature of the electrothermal furnace is maintained for a preset time. Thereafter, the illustrated embodiment permits the furnace to be advanced to a higher temperature for a preset amount of time in order to clean out deposits of the analyte from the furnace 2 and the ICP torch 4. Removal of the analyte deposits is important so that subsequent tests are not affected by prior tests.

Although in the illustrated embodiment an ion detector 19 is used in the third stage 17 of the vacuum chamber 11, the concept of the proposed invention would remain unchanged if some other means or location were chosen to detect the rate of analyte emerging from the electrothermal furnace 2. For example, the current in the quadrapole mass spectrometer 18 may vary with the current of ionized analyte in the ion flow 16 emerging from the ion lens system 13. This current variation may be detected and used as the input to the feedback controller circuitry 20. Alternatively, the ion flow 16 itself could be passed directly through a coil or other means for detecting the electric current carried by the ion flow, which would vary with the amount of ionized analyte in the flow.

Figure 3:
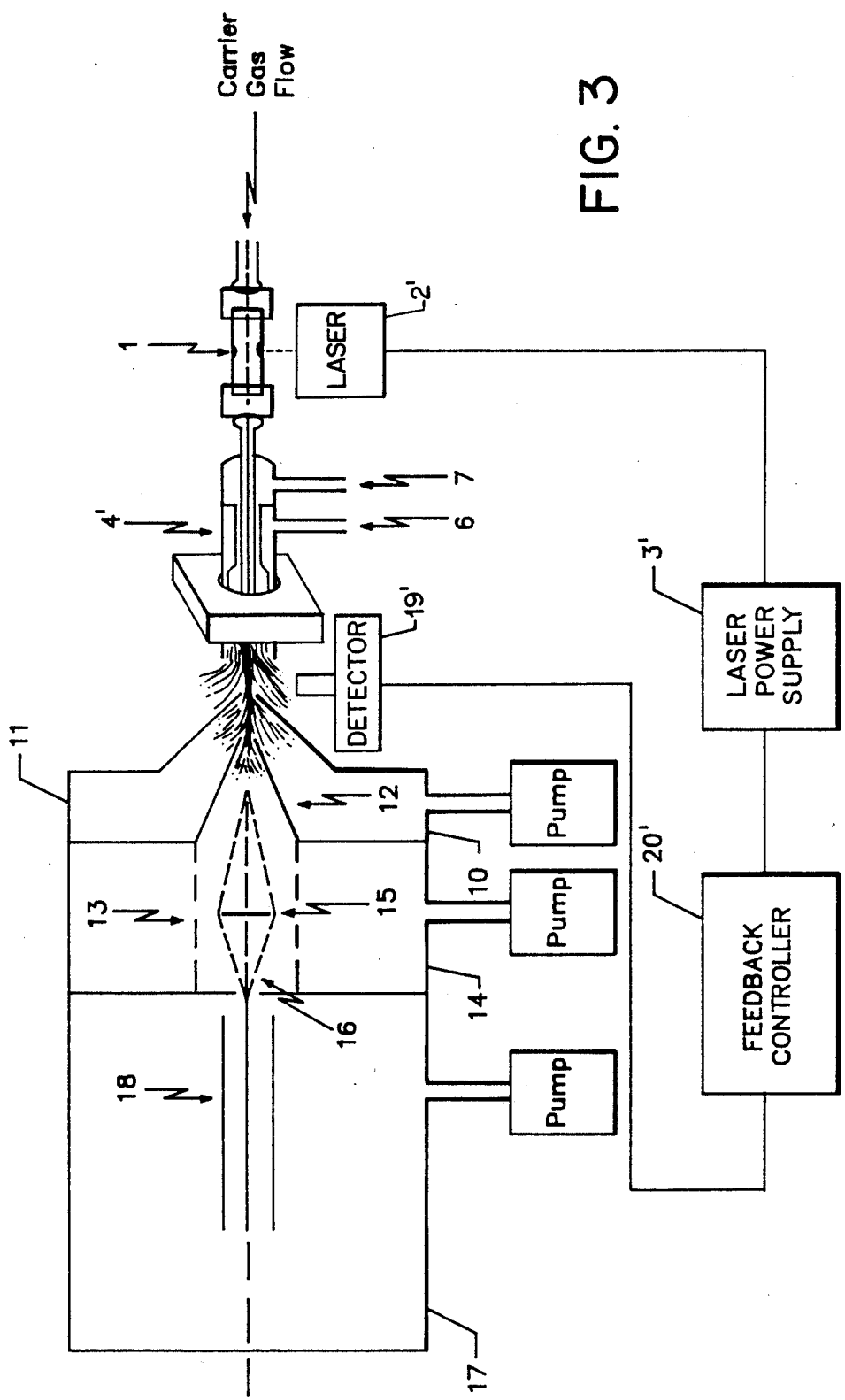
FIG. 3 is a schematic diagram of a microwave induced type plasma emission spectroscopic instrument employing an alternative embodiment of the inventive demand modulated atomization apparatus and method of the present invention.

Another possibility for detecting the flow rate of analyte in the instrument may make use of photodetectors or spectral detectors to determine the brightness of the photon beam from the ICP torch 4 at any point in the system up to the photon stop shield 15. Another measurement technique would be to analyze the emission spectra of the plasma flow 8 emerging from the ICP torch 4 prior to impingement upon the sampler cone 9. The spectral intensity should vary with the amount of analyte in the plasma flow 8. FIG. 3 illustrates a system in accordance with an alternative embodiment utilizing alternative detectors as represented generally by the detector 19' of FIG. 3.

Still another measurement technique would be to monitor the plasma flow 8 potential, which would vary as foreign material (i.e., analyte) is added to the plasma.

Another means for detecting the analyte flow rate would be to measure the back electromotive force generated in the RF inductive coils 5 surrounding the ICP torch 4 as the charged plasma flow passes through the coils with varying amounts of analyte ions, or to monitor the RF tuning network coupled to the inductive coils 5 for tuning changes caused by varying amounts of analyte ions passing through the coils. This last technique would allow the use of alternative plasma sources, such as microwave induced plasmas, with little or no change in the atomizer feedback loop. Still another detection means would be to directly measure the flow of carrier gas and analyte passing from the electrothermal furnace 2 to the ICP torch 4.

Thus, the method taught by the present invention of feedback control of the electrothermal furnace 2 is not limited to any one particular detection means or placement, so long as a fairly accurate determination can be made of the amount of analyte contained within the analyte gas flow, plasma flow, or ion flow. This rate is then provided to the feedback control circuit 20 described below, or to an equivalent feedback control means.

Figure 2:
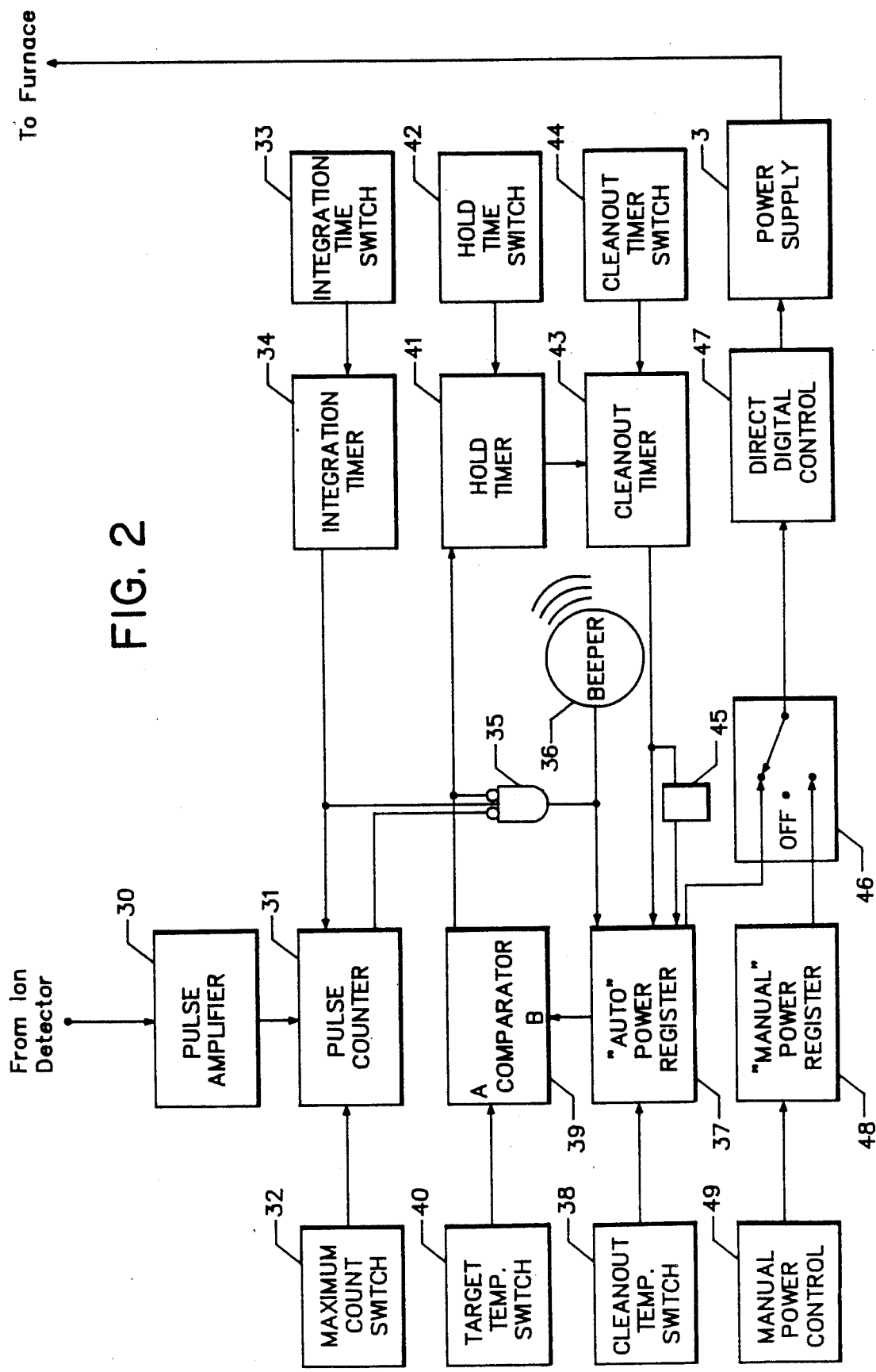
FIG. 2 is a schematic diagram of one embodiment of an electronic feedback control circuit for use in conjunction with the present invention.

FIG. 2 is a schematic diagram of one embodiment of the feedback controller circuit 20 of FIG. 1. The output of the ion detector 19 in FIG. 1 is coupled to a pulse amplifier 30, the output of which is coupled to a pulse counter 31 (which may be simply an integrated circuit counter circuit). A maximum count switch 32 is provided to controllably set the initial count value for the pulse counter 31. That is, an operator may enter a desired ion count in the maximum count switch 32 (which may be a set of thumbwheel switches, for example), and the pulse counter 31 will generate an output signal when the number of counted pulses from the pulse amplifier 30 reaches the preset value.

An integration time switch 33 permits an operator to select an averaging period, the value of which is coupled to an integration timer 34. The output of the integration timer 34 is coupled to the pulse counter 31 and causes the pulse counter 31 to be reset to zero at the end of the preset integration time period.

If the number of ion counts counted by the pulse counter 31 during the integration time period is less than the value set on the maximum count switch 32, the pulse counter 31 outputs a signal to an AND gate 35, which is only enabled during the integration period set by the integration timer 34. If the pulse counter 31 has not reached the preset maximum count by the end of the integration period, the output of the pulse counter 31 will be zero, and hence a positive signal will be generated by the AND gate 35. The output of the AND gate 35 is coupled to a beeper 36 to give an audible indication that the desired ion flow rate has not been obtained, and that the power to the electrothermal furnace will be increased.

The output of the AND gate 35 is also coupled to an automatic power register 37. The automatic power register 37 is an incrementable register that is incremented by the output of the AND gate 35. During the testing phase of operation, the value stored in the automatic power register 37 is coupled to a comparator 39, which is also coupled to a target temperature switch 40, the value of which is set by an operator. The comparator 39 compares the value set on the target temperature switch 40 with the actual value stored in the automatic power register 37, and outputs a signal if the two values are equal.

The output of the comparator 39 is coupled to the enable input of a hold timer 41, an input of which is coupled to a hold time switch 42. An operator may enter a desired hold time by means of the hold time switch 42. The output of the comparator 39 also disables AND gate 35, preventing further incrementing of the automatic power register 37. This allows the electrothermal furnace 2 to be maintained at the desired target temperature for the period of time set by the hold time switch 42.

When the hold timer 41 times out, it outputs a signal to the enable input of a cleanout timer 43. A cleanout timer switch 44 coupled to an input of the cleanout timer may be set by an operator to store the desired cleanout time period. After the cleanout timer 43 is enabled by the output signal from the hold timer 41, it generates a signal which is coupled to the load input of the automatic power register 37. This signal loads the cleanout temperature value set on a cleanout temperature switch 38 into the automatic power register 37. The cleanout temperature switch 38 is used to set the temperature to which the electrothermal furnace 2 is to be raised at the end of a test cycle, in order to clean out analyte residue from the electrothermal furnace 2 and the ICP torch 4.

After the cleanout timer 43 has timed out, a reset signal is generated which resets the automatic power register 37 to a zero value. This may be done, for example, by a one-shot circuit 45 that is activated on the falling edge of the clean out time 43 output signal.

The value stored in the automatic power register 37 at any time may be coupled by a switch 46 to a direct digital control circuit 47. Also coupled to the direct digital control circuit 47 is a manual power register 48, the value of which may be set by means of a manual power control 49. This allows complete non-automatic control of the system by manually changing the value stored in the manual power register 48 and coupling the output of that register to the direct digital control 47 by means of the switch 46.

The direct control signal 47 comprises a rate multiplier circuit (which may be, for example, one or more CD4089B integrated circuits manufactured by Sylvania Electronics Components Group). This circuit translates a numeric input value to a symmetric pulse train within a fixed time frame. Thus, higher numeric values will create a larger number of symmetric pulses within the same amount of time. These pulse trains are coupled to the controllable power supply 3, the control for which is provided by a triac driving circuit. Such a driving circuit takes as an input a pulse train, and controllably switches the power supply on and off as a function of the pulse train frequency. Higher numeric input values to the direct digital control circuit 47 will generate more pulses within the same amount of time, thus causing the power supply 3 to remain on for a longer period of time. This permits current to be supplied to the electrothermal furnace 2 for a longer period of time, thus raising its temperature.

Thus, the cycle of operation is that the automatic power register 37 is incremented every time the pulse counter 31 fails to count the ion count rate set on the maximum count switch 32 during the integration time period set into the integration timer 34. Incrementing continues until the ion count rate reaches the desired value, or the value in the automatic power register 37 reaches the preset hold temperature value. The value of the automatic power register 37 ultimately controls the temperature of the electrothermal furnace 2.

After the hold period set in the hold timer 41 ends, a cleanout temperature value is loaded from the cleanout temperature switch 38 into the automatic power register 37. The temperature of the electrothermal furnace 2 will thus be raised to the clean out temperature for the period set in the cleanout timer 43, after which the entire system will reset itself.

While this invention had been described with reference to an illustrated embodiment, it is not intended that this description be construed in a limiting sense. Various modifications of the illustrated embodiment, as well as other embodiments of the invention, will be apparent to persons skilled in the art upon reference to this description. For example, the power supply 3 may be of a variable output voltage, a variable output current, or a variable output frequency type. By suitably interfacing the feedback controller circuit 20 output, any of these types of power supplies could be accommodated. Further, means other than an inductively coupled plasma torch may be used to produce an analyte-bearing plasma, such as a microwave-induced plasma torch, as represented generally at 4' in FIG. 3. The feedback control means of the present invention could also be readily adapted to control a direct form of plasma generation, such as a laser ablation system, as indicated generally at 2' in FIG. 3. In such a system, a laser directly thermally atomizes an analyte, which may then be passed to a plasma torch. The power of the laser could be controlled by the inventive feedback means to regulate the amount of analyte being tested. Moreover, although reference has been made to analyte flow, plasma flow, and ion flow, the underlying factor that is being controlled by the present invention is the amount of analyte being measured by spectroscopic means. Thus, the present invention could be readily adapted for use in a plasma-based spectroscopic system where little or no gaseous flow occurs. It is therefore contemplated that the appended claims will cover any modifications or embodiments as fall within the true scope of the invention.

I claim:

1. A demand modulated atomization system for use in a spectral analysis system having an analyte measurement means for measuring desired spectral characteristics of an analyte in a plasma, the system comprising:
   a. thermal atomization means for thermally atomizing the analyte;
   b. a plasma generation means coupled to the output of the thermal atomization means, for creating a plasma containing the analyte;
   c. a spectral detection means for measuring the content of the atomized analyte; and
   d. a feedback means coupled to the spectral detection means and the thermal atomization of analyte to a preset limit, and controlling the thermal atomization means to regulate the rate of analyte atomization so as to cause the measured content of analyte to obtain an approximately fixed relationship to the preset limit.

2. The demand modulated system of claim 1 wherein the spectral detection means measures the amount of analyte in the plasma.

3. The demand modulated system of claim 1 wherein the spectral detection means is an ion detector.

4. The demand modulated system of claim 1 wherein the spectral detection means measures the brightness of the analyte-containing plasma.

5. The demand modulated system of claim 1 wherein the spectral detection means measures the brightness of the atomized analyte.

6. The demand modulated system of claim 1 wherein the spectral detection means measures the spectral intensity of the analyte in the plasma.

7. The demand modulated system of claim 1 wherein the spectral detection means measures the spectral intensity of the atomized analyte.

8. The demand modulated system of claim 1, wherein the plasma generation means is an inductively coupled type.

9. The demand modulated system of claim 1, wherein the plasma generation means is a microwave induced type.

10. The demand modulated system of claim 1 wherein the feedback means includes:
    a. a limit setting means for storing a desired preset count limit;
    b. a counter comparison means, coupled to the spectral detection means and the limit setting means, for counting the amount of analyte detected during a period of time and comparing the count to the preset count limit;
    c. a control means, coupled to the counter-comparison means and the thermal atomization means, for regulating the temperature of the thermal atomization means in response to the output of the counter-comparison means.

11. The demand modulated system of claim 1 wherein the thermal atomization means comprises a laser for laser ablating the analyte.

12. A demand modulated atomization system for use in a spectral analysis system having a spectral measurement means for measuring desired spectral characteristics of an analyte in a plasma, the system comprising:
    a. a temperature controllable electrothermal furnace for thermally atomizing the analyte;

b. a plasma generation means coupled to the output of the furnace, for creating a plasma containing the analyte;

c. an ion detection means coupled to the plasma generation means for measuring the content of the atomized analyte in the plasma; and d. a feedback means coupled in the ion detection means and the furnace, for comparing the measured content of analyte to a preset limit and controlling the temperature of the furnace to regulate the rate of analyte atomization in the furnace so as to cause the measured amount of analyte to obtain an approximately fixed relationship to the preset limit.

13. A demand modulated electrothermal atomization spectral analysis system including:

a. a temperature controllable electrothermal furnace for thermally atomizing an analyte;

b. a plasma generation means coupled to the furnace, for creating a plasma containing the analyte;

c. a spectral measurement means coupled to the plasma output of the plasma generation means, for measuring desired spectral characteristics of the analyte in the plasma;

d. a photon detector for measuring the intensity of photons emitted from the plasma output of the plasma generation means; and e. a feedback means coupled to the photon detector and the furnace, for comparing the measured intensity of photons to a preset limit and controlling the temperature of the furnace to regulate the rate of analyte atomization so as to cause the measured content of atomized analyte to obtain an approximately fixed relationship to the preset limit.

14. The demand modulated system of claim 13, wherein the spectral measurement means includes means for measuring atomic fluorescence spectral characteristics.

15. The demand modulated system of claim 13, wherein the spectral measurement means includes means for measuring atomic mass spectral characteristics.

16. The demand modulated system of claim 13, wherein the spectral measurement means includes means for measuring atomic emission spectral characteristics.

17. A demand modulated electrothermal atomization system for use in a spectral analysis system having an analyte measurement means for measuring desired spectral characteristics of an analyte in a plasma, the system comprising:

a. a controllable electric power supply;

b. an electrothermal furnace coupled to the power supply, for thermally atomizing the analyte;

c. an analyte detection means for measuring the amount of atomized analyte;

d. a plasma generation means coupled to the output of the furnace, for creating a plasma containing the analyte; and e. a feedback means coupled to the analyte detection means and the power supply, for comparing the measured amount of analyte to a preset limit and controlling the output of the power supply to regulate the rate of analyte atomization in the furnace so as to cause the measured amount of analyte to approximately equal the preset limit.

18. A demand modulated electrothermal atomization spectral analysis system including:

a. a controllable electric power supply;

b. an electrothermal furnace coupled to the power supply, for thermally atomizing an analyte;

c. an analyte detection means for measuring the amount of atomized analyte;

d. a plasma generation means coupled to the output of the furnace, for creating a plasma containing the analyte;

e. an analyte measurement means coupled to the output of the plasma generation means, for measuring desired spectral characteristics of the analyte in the plasma; and f. a feedback means coupled to the analyte detection means and the power supply, for comparing the measured amount of analyte to a preset limit and controlling the output of the power supply to regulate the rate of analyte atomization so as to cause the measured amount of analyte to approximately equal the preset limit.

19. A method for regulating the amount of analyte in a spectral analysis system having an analyte measurement means for measuring desired spectral characteristics of an analyte in a plasma, a temperature controllable means for thermally atomizing the analyte, a plasma generation means coupled to the output of the thermal atomization means for creating a plasma containing the analyte, an analyte detection means for measuring the amount of atomized analyte, and a feedback controller coupled to the analyte detection means and the thermal atomization means wherein the feedback controller performs at least the steps:

a. comparing the amount of analyte measured by the analyte detection means to a preset limit; and b. controlling the temperature of the thermal atomization means to regulate the rate of analyte atomization in the thermal atomization means so as to cause the measured amount of analyte to obtain an approximately fixed relationship to the preset limit.

* * * * *